United States Patent
Heeres et al.

(10) Patent No.: US 7,880,067 B2
(45) Date of Patent: Feb. 1, 2011

(54) POTATOES WITH INCREASED PROTEIN CONTENT

(75) Inventors: Paul Heeres, Valthermond (NL); Nicolaas Clemens Maria Henricus de Vetten, Groningen (NL)

(73) Assignee: Cooperatie AVEBE U.A., Ja Veendam (NL)

( * ) Notice: Subject to any disclaimer, the term of this patent is extended or adjusted under 35 U.S.C. 154(b) by 1103 days.

(21) Appl. No.: 10/537,037

(22) PCT Filed: Dec. 2, 2003

(86) PCT No.: PCT/NL03/00851

§ 371 (c)(1),
(2), (4) Date: Nov. 25, 2005

(87) PCT Pub. No.: WO2004/049785

PCT Pub. Date: Jun. 17, 2004

(65) Prior Publication Data

US 2006/0123513 A1 Jun. 8, 2006

(30) Foreign Application Priority Data

Dec. 4, 2002 (EP) .................. 02080109

(51) Int. Cl.
*A01H 1/00* (2006.01)
*A01H 1/02* (2006.01)
(52) U.S. Cl. .................. 800/317.2; 800/260
(58) Field of Classification Search .................. 800/260, 800/317.2
See application file for complete search history.

(56) References Cited

FOREIGN PATENT DOCUMENTS

WO WO 01/48230 A2 7/2001

OTHER PUBLICATIONS

Poehlman et al. 1995. Breeding Field Crops, 4th ed.*
Jacobsen et al. 1989. Euphytica 44: 43-48.*
Jacobsen et al. 1991. Euphytica 53: 247-253.*
Poehlman et al. Breeding Potato, In Breeding Field Crops, Chapter 21, pp. 419-433, 1995.*
Farran et al. 2002. Transgenic Research 11: 337-346.*
Jacobsen et al. Euphytica 44: 43-48, 1989.*
Jacobsen et al. Euphytica 53: 247-253, 1991.*
Poehlman et al. Breeding Potato, In Breeding Field Crops, Chapter 21, pp. 419-433, 1995.*
Farran et al. Transgenic Research 11: 337-346, 2002.*
Hovenkamp-Hermelink, J.H.M., et al., "Isolation of an amylose-free starch of the potato (*Solanum tuberosum* L.)", *Theor Appl Genet.* 1987, 75:217-221.
Jacobsen, E., et al., "Introduction of an amylose-free (*amf*) mutant into breeding of cultivated potato, *Solanum tuberosum* L.", *Euphytica* 1991, 53:247-253.
Kortstee, Anne J., et al., "Expression of *Escherichia coli* branching enzyme in tubers of amylose-free transgenic potato leads to an increased branching degree of the amylopectin", *The Plant Journal* 1996, 10(1):83-90.

* cited by examiner

*Primary Examiner*—Medina A. Ibrahim
*Assistant Examiner*—Keith O. Robinson
(74) *Attorney, Agent, or Firm*—Hoffmann & Baron, LLP

(57) ABSTRACT

The invention relates to the breeding and selection of potatoes. The invention provides a potato plant or part derived thereof having at least one amf-allele said potato plant or part further provided with an increased capacity to store a protein as characterized by an increased protein content of its tubers. Furthermore, the invention provides a method for breeding and selecting a potato with an increased capacity to store a protein comprising crossing a first parent potato with at least one amf-allele with a second parent potato without an amf-allele, and selecting progeny for the presence of at least one amf-allele with a protein content of its tubers higher than detected in said first parent or said second parent.

9 Claims, 4 Drawing Sheets

POTATOES WITH INCREASED PROTEIN CONTENT

This application is the U.S. National Phase of International Application Number PCT/NL2003/000851 filed on 2 Dec. 2003, which is incorporated herein by reference.

BACKGROUND OF THE INVENTION

The invention relates to the breeding and selection of potatoes.

Apart from being an important staple food, potato is classically the raw material for industrial production of starch from potato tubers. Furthermore, these days, the industrial harvest of potato protein from potato tubers, earlier seen as a quantité négligeable attracts more attention considering the increased value given to vegetable protein sources, for example for animal food, if only as a side product accompanying starch production. Where, chemically, potato starch in potato tubers essentially consists of two components: amylopectin and amylose in a proportion of approximately 80% to 20%, potato proteins in tubers essentially consist of protease inhibitors that help protect the tuber against disease such as parasite infestations or fungal or bacterial rot and storage proteins such as patatin in a proportion of approximately 60% to 40%.

For various reasons, starch producers prefer potatoes with different ratios of amylopectin and amylose. An earlier induced gene mutation in potatoes that affects the synthesis of the enzyme granule bound starch synthase (GBSS), and the subsequent molecular cloning of this gene (Hovenkanp-Hermelink et al., 1987, Theor. Appl. Genet. 75:217-221; Visser et al., 1989, Plant Science 64:185-192) has opened possibilities for altering the starch composition of potatoes—either through established breeding methods or through modern techniques of genetic manipulation.

The GBSS mutation in potato is similar to the so-called waxy (wx) mutation in maize and prevents the production of amylose, when expression or specific function of the GBSS protein is absent. Therefore, this mutation has been designated as amylose-free (amf) mutant of potato. Herein, the amf-gene mutation stands for a modification of the GBSS-gene that leads to a complete functional loss of GBSS-activity, notwithstanding that GBSS-like gene products, without the specific activity, may still be expressed from the gene's transcripts in question, whereby the Amf-gene stands for a gene from which gene products with GBSS-activity can still be obtained. The amf-gene character is determined by a monogenic mendelian recessive gene, the phenotype of which can be detected in various plant parts such as columella cells of root tips, tubers, plastids in the stomatal guard cells and in microspores (Jacobsen et al., 1989, Euphytica 44:43-48). When these parts are stained with a potassium iodine solution (Lugol), starch is stained red in mutants and dark blue in the wild type.

Unlike many other phenotypic genetic markers, the mutated or functionally deleted GBBS- or amf-gene offers certain special advantages for genetic analysis as well as for breeding. For example, the progeny can be classified at a very early seedling stage as well as in adult plants, through pollen staining, homo- and heterozygotes can be unambiguously classified: the dosages 2-4 of the mutant allele in a tetraploid can be easily detected through the ratios 5:1, 1:1 and 0:1 in stained pollen samples; different types of 2n-gametes in diploid clones can be detected and their influence on the phenotype and genotype of tetraploid from 4x*2x crosses can be predicted.

Prospects of using the material in conventional as well as in analytic breeding of potato have since the development of the amf-gene potato mutant of Hovenkamp-Hermelink been opened. A disadvantage for breeding is the recessive nature of amf, which complicates the combination of this character with other agronomic traits at the tetraploid level.

Therefore, the analytic breeding method advocated by Chase (1963, J. Genet. Cytol. 5:359-364), which involves breeding of potato at the diploid level and returning to the tetraploid condition through the use of 2n-gametes, could be of considerable value for breeding amf-varieties. The aim of such investigations are at least two fold: a. to combine amfamf and Amfamf genotypes with that of 2n-gamete formation, and b. to create fertile, nulliplex clones as basic material for breeding amylose-free potatoes. On the other hand, development of suitable diploid material that produces high frequencies of 2n-pollen and 2-eggs would also open the way for unilateral and bilateral sexual polyploidization (Mendiburu and Peloquin, 1976, Theor. Appl. Genet. 48:137-143). Such diploid breeding material may be homozygous (amfamf) or heterozygous (Amfamf), because in both cases selection can be carried out based on pollen phenotype.

SUMMARY OF THE INVENTION

The invention relates to the breeding and selection of potatoes. Surprisingly, it was found herein that potatoes with at least one amf-allele background have a distinct phenotypic advantage when compared with potatoes having a similar genetic background lacking the amf-gene. One such advantage relates to protein content. Genotypes that are nulliplex for the Amf-allele, i.e. for diploid plants the amfamf (aa) and for tetraploid plants the amfamfamfamf (aaaa) genotypes display said advantage even stronger.

The invention provides a potato plant or part derived thereof (such as a cell, a protoplast, a tuber, an embryo, a seed or an explant) having at least one amf-gene said potato plant or part further provided with an increased capacity to store a protein (herein also identified as a high protein potato) as characterized by a total raw protein content of its tubers (preferably as determined in the potato juice derived thereof) at least 1-9% m/m, more preferred at least 2.3% m/m, most preferred at least 2.7% m/m. Within a potato homozygous for the amf-allele as provided herein, i.e. an amylose-free high protein potato, such increased capacity to store protein is most fully developed. The inventors have gathered the surprising insight that depriving a potato of GBSS-activity allows for increasing protein storage in said potato, provided it has the genetic capacity to produce increased, or at least sufficient, amounts of said protein. Potatoes comprising an amf-allele have essentially higher protein storage capacity than potatoes of otherwise similar genetic background having no amf-gene. Potatoes homozygous for the amf-allele are, speaking from the viewpoint of protein storage, preferred.

Originally, the amf-mutation was induced in a monohaploid which had been selected only for flowering (Hovenkamp-Hermelink et al., 1987, ibid) but not for fertility and agronomic characters. Therefore, in order to incorporate this recessive mutant in other potatoes the inventors crossed the diploid genotype derived from the monoploid mutant clone with agronomically more desirable clones which, however, have the wild type of the Amf gene. As a first step in this process, fertile diploids that are homozygous for the mutant character (amfamf), were produced. When these diploids are somatically doubled through in vitro adventitious shoot regeneration, the resulting tetraploids proved to be less fertile (both male and female). However the 4x plants obtained through meiotic doubling—using 4x×2x crosses—gave rise to fertile nulliplex tetraploids. Thus, in spite of high levels of sterility and expression of lethal factors in the initial stages, more fertile and vigorous diploid and tetraploid breeding material were created with the desired amf-genotypes. Availability of vigorous, fertile and agronomical useful tetraploid genotypes than led to conventional breeding of amf-mutants of potato. It was than surprisingly found that amf-mutants, resulting from crosses with wild-type potatoes had increased storage capacity for proteins in their tubers, these days considered an economically desirable trait.

It is preferred that said high total raw protein content is also reflected in the amount of protein that can be harvested, e.g. from the tubers. Such measure is given by identifying the fraction of coagulating protein available for harvest, as further explained in the detailed description. The invention also provides a potato plant or part derived thereof (such as a cell, a protoplast, a tuber, an embryo, a seed or an explant) having at least one amf-gene said potato plant or part further provided with an increased capacity to produce harvestable protein as characterized by a total coagulating protein content of its tubers (preferably as determined in the potato juice derived thereof) at least 0.9%, more preferred at least 1.2%, most preferred at least 1.5%. Considering that high protein levels are these days often more profitable than high starch levels, the invention also provides a high protein potato (i.e. with more than 1.2%, preferably more than 1.5% coagulating protein in its tubers) characterized in that its tubers essentially show a coagulating protein versus starch ratio of at least 45 kg/ton, more preferred of at least 90 kg/ton.

Furthermore, the invention provides a high-protein potato according to the invention characterized in that it is a transgenic potato, for example provided with a gene or gene encoding for a heterologous protein, for example with the purpose to provide a high protein potato according to the invention additionally provided with increased levels of essential amino acids. It is preferred that such a heterologous protein comprises a heterologous protein rich in essential amino acids. About half of the 20 amino acids found in proteins can be made by vertebrates; the others must be supplied in the diet. For this reason, the latter are called essential ammo acids. These include the strictly essential amino acids which are lysine, leucine, isoleucine, valine, phenylalanine, methionine, threonine and tryptophan. Additionally, tyrosine and cysteine, although they are not strictly essential, must be considered as such, since they are synthesised only from essential amino acids: tyrosine from phenylalanine and cysteine from methionine. In particular, humans and other monogastric animals cannot synthesise the essential amino acids and need to obtain these from their diet. The diet of humans and livestock is largely based on plant material. However, several of these essential amino acids are often only present in low concentrations in crop plants, which mainly constitute said plant based diets. In particular, lysine, threonine, methionine or tryptophane often lack in such diets. Dietary proteins are often not nutritionally equivalent, which correlates with the amino acid composition of the different proteins. Feeding a diet that provides an inadequate amount of one of the essential amino acids leads to negative nitrogen balance, since the normal catabolism of proteins continues, but new synthesis for replacement is limited by the relative lack of the essential amino acid. This occurs even when the total dietary intake of protein is apparently adequate. The extent to which a dietary protein can be used for the synthesis of tissue proteins is limited by the content of the essential amino acid that is present in an amount relative to the requirement. This is the limiting amino acid of that protein. Now that a high protein potato is provided it is beneficial to age this for the expression and storage of valuable proteins. The invention furthermore provides a transgenic potato cell with at least one amf-allele having been provided with a nucleic acid encoding a proteinaceous substance, a sink protein. In a preferred embodiment, said cell accumulates said sink protein up to more than 2%, preferably 4%, or even more than 5% to more than 7% of the total protein content of said cell. The protein preferably contains a high content of essential amino acids (preferably methionine, cysteine, lysine, threonine, or tryptophane). In a preferred embodiment, the invention provides a high protein potato according to the invention comprising a heterologous protein rich in essential amino acids such as listed in Table 4.

The invention also provides a method for breeding and selecting a potato with an increased capacity to store a protein comprising crossing a first parent potato with at least one amf-gene with a second parent potato without an amf-allele, and selecting progeny for the presence of at least one amf-allele and for a protein content of its tubers higher than detected in said first parent or said second parent. It is preferred that progeny is selected or a protein content of its tubers higher than detected in said first parent and said second parent. Of course, the storage of proteins being most fully enhanced in amylose-free plants, it is most preferred to select progeny homozygous for the amf-allele.

In a preferred embodiment, the invention provides a method for breeding and selecting a potato with an increased capacity to store a protein comprising crossing a first parent potato with at least one amf-allele with a second parent potato without an amf-gene, and selecting progeny (preferably homozygous for the amf-allele) by testing it or the presence of at least one amf-gene and testing it for total raw protein content with a method, such as the Kjeldahl method as described herein, to determine total raw protein content of its tubers and selecting progeny with a total raw protein content higher than detected in said first parent or said second parent, said method preferably further comprising selecting progeny with a total raw protein content of its tubers higher than detected in said first parent and said second parent.

In a further preferred embodiment, the invention provides a method for breeding and selecting a potato with an increased capacity to produce harvestable protein comprising crossing a first parent potato with at least one amf-allele with a second parent potato without an amf-allele, and selecting progeny (preferably homozygous for the amf-allele) by testing it for the presence of at least one amf-allele and testing it for coagulating protein content with a method comprising determining total raw protein and total soluble raw protein remaining in solution after a protein coagulation procedures, such as immersion in a boiling water bath as described herein, to determine or calculate total coagulating protein content of its tubers and selecting progeny with a total coagulating protein content higher than detected in said first parent or said second parent, said method preferably further comprising selecting progeny with a total coagulating protein content of its tubers higher than detected in said first parent and said second parent.

Furthermore, the invention provides a potato selected with a method according to the invention, use of a potato as provided herein for the industrial production of starch and/or protein and use of a potato as provided herein in breeding and selection programmes of potatoes. In particular, the invention provides use of a potato plant or part derived thereof having at least one amf-allele in a breeding and selection programme directed at providing potatoes with an increased protein content.

Figure 1:
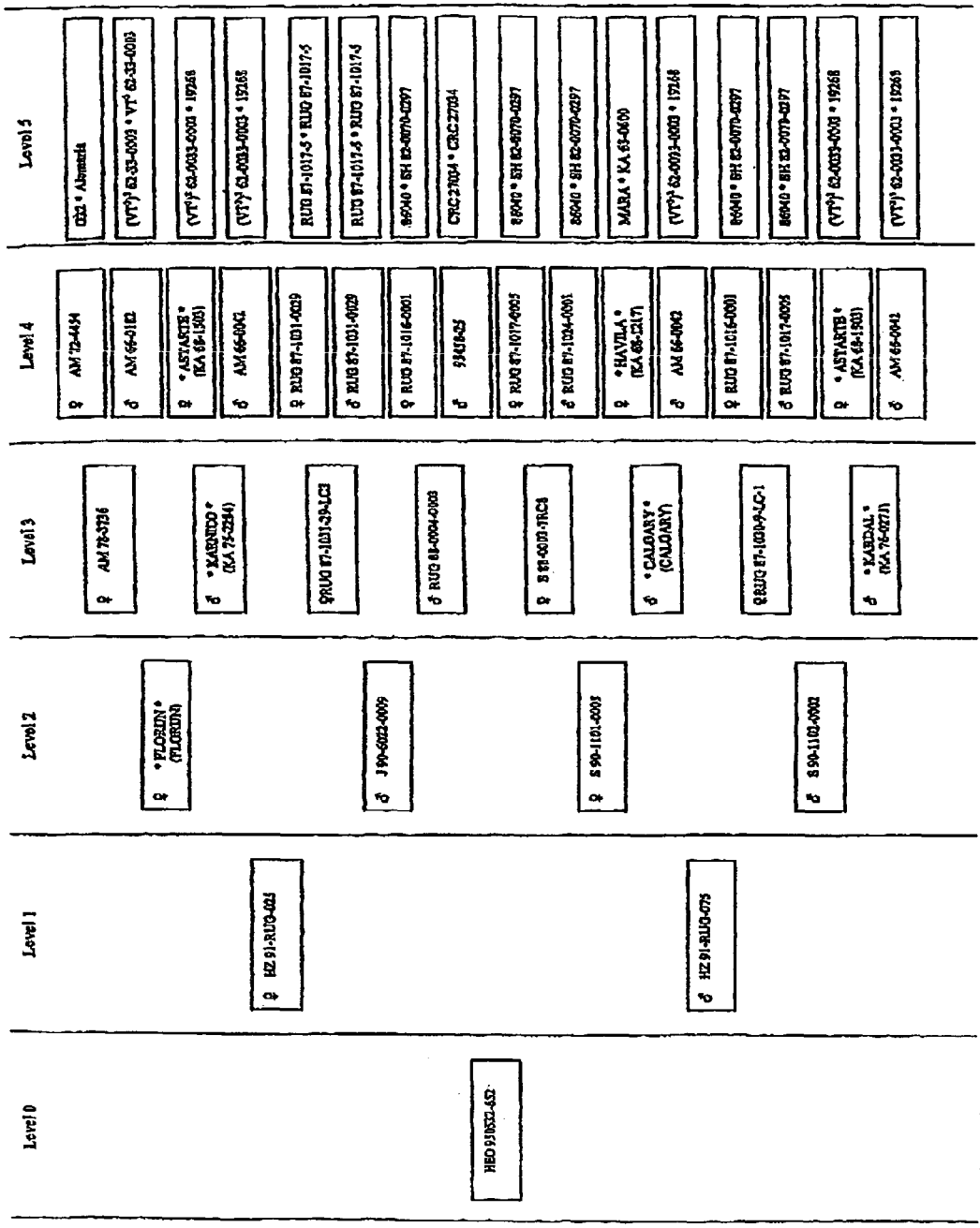
FIGS. 1 to 4.
Figure 2:
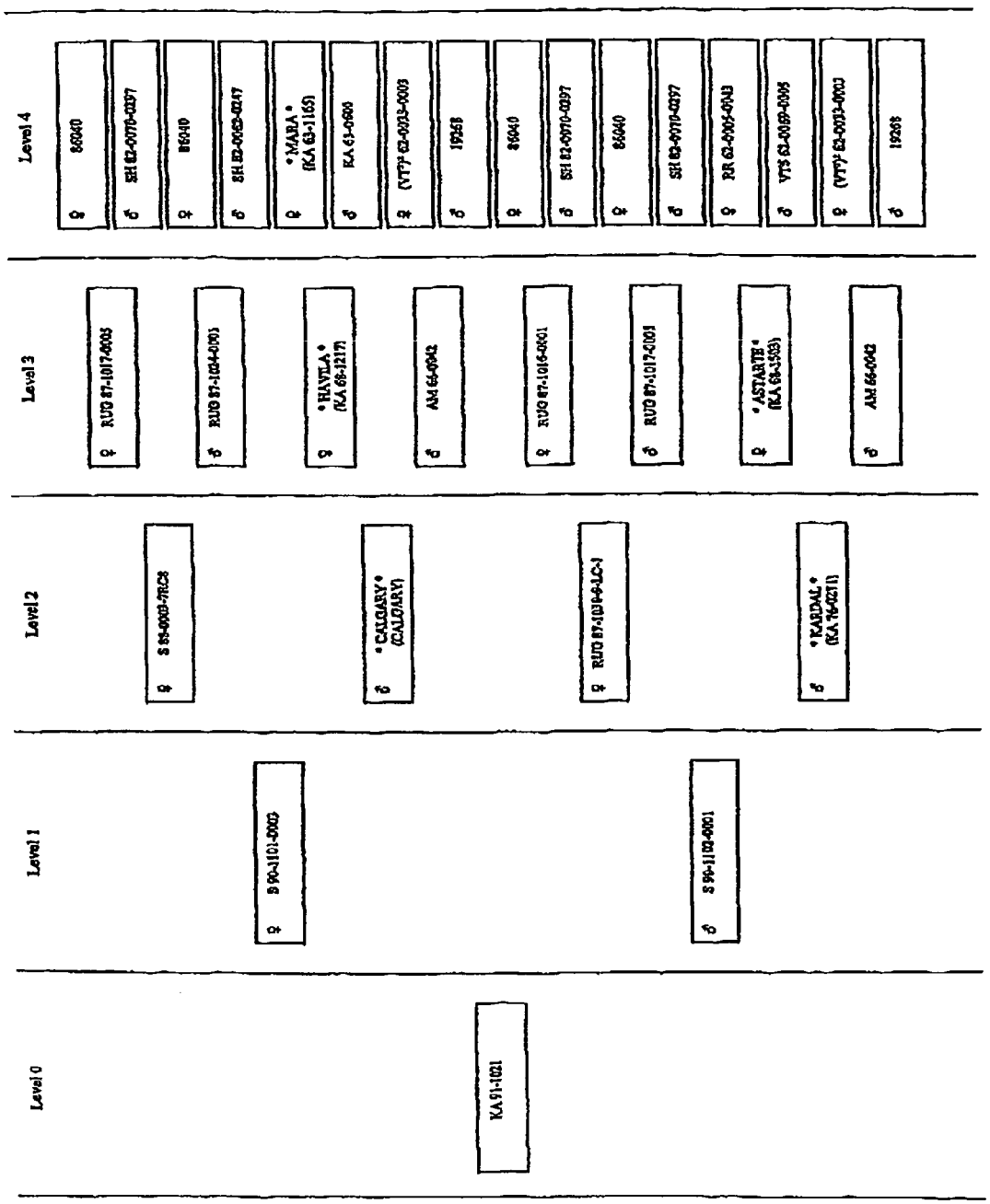
Figure 3:
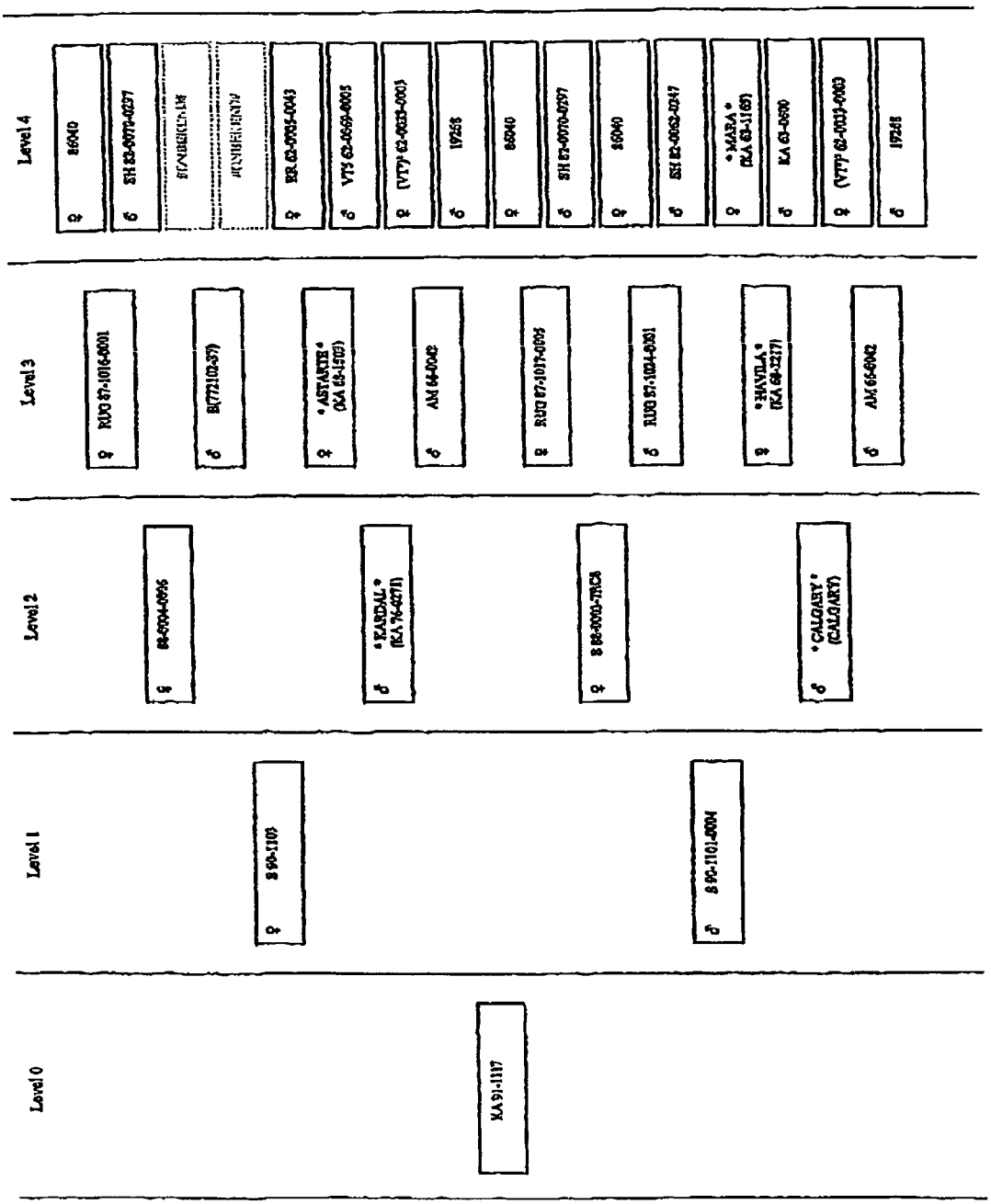
Figure 4:
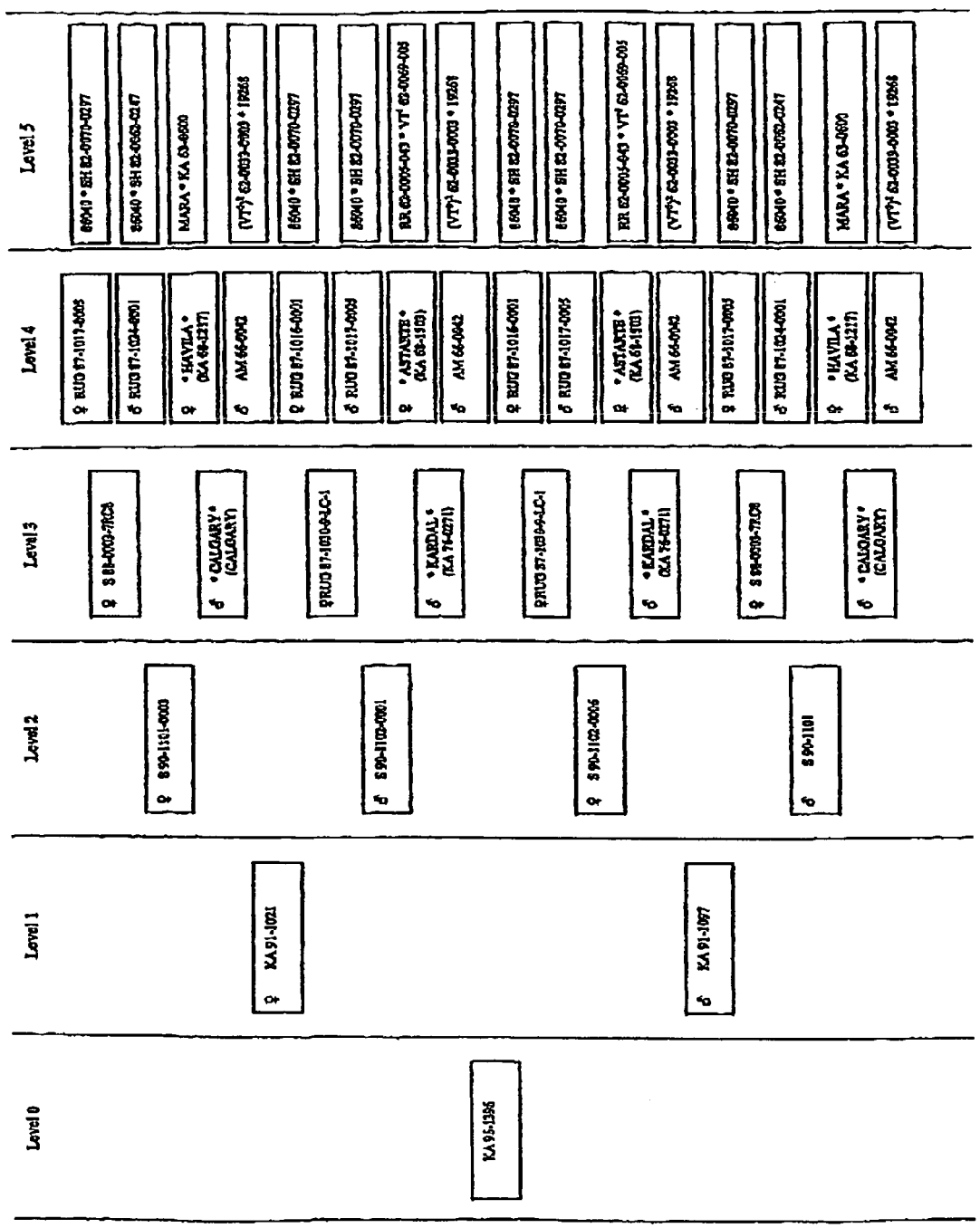

Examples of breeding schemes for breeding and selecting potatoes

DETAILED DESCRIPTION OF THE INVENTION

Using an amylose-free (amf)mutant of diploid potato (*Solanum tuberosum*), diploid and tetraploid clones with different genotypes at the amf-locus were produced. In order to make use of the diploid material in analytic breeding of amf-potatoes, clones were selected that produced considerable frequencies of 2n-pollen and 2n-eggs. Successful attempts were made to select normal synaptic as well as desynaptic clones producing 2n-gametes. When for example microspores are stained with a potassium iodide solution (Lugol), starch is stained red in mutants (comprising only the amf-gene) and dark blue in the wild type (comprising only the Amf-allele). Based on the phenotype of starch in the microspores, tetraploid clones with nulliplex, simplex, duplex, triplex and quadriplex genotypes at the Amf-locus were selected. We investigated starch properties and protein content in various parts of the mutant potato plant. Starch composition and protein content in tubers turned out to be an easily scorable feature. It allows in breeding programmes for amylose-free potatoes an early assessment of starch and/or protein composition in the prospective plants or parts thereof.

Plant material. Monoploid amylose-free (amf) clone 86.040 and the parent clone AM79.7322 are described in Hovenkamp-Hermelink et al. (1987, ibid). Doubled amf-plants were obtained by adventitious shoot regeneration on leaf explants, which were taken from in nitro propagated shoots of monoploid 86.040. After root induction in $MS_{30}$ (Murashige & Skoog, 1962, Physiol. Plant 15:473-497) (MS) medium supplemented with 30 g/l sucrose) a number of these diploid amf-plants were transferred into a glasshouse, at 19° C. at day: 17° C. at night and 16 h daylength, in sterilized leaf containing soil. For better flowering, part of the doubled plants was grafted onto tomato rootstock. Pollen fertility was estimated, after aceto carmine staining. For the crosses, a variety of wild-type potato pollen was used. The crosses were made on open flowers of diploid (2x) clones of 86.040. The wild-type potato clones had been selected for good male an finale fertility and 2n-gametes (unreduced gamete) production in male and female parents.

This resulted in breeding material with better fertility both on male and female side giving opportunity to make crosses with more advanced diploid breeding material. From these crosses diploid as well as tatraploid progeny (4x) was obtained. Diploid material was segregating for the amf-allele, resulting in 25% homozygous plants, which could be selected by colouring the tubers with a iodine solution. Also some tetraploid progeny could be obtained as a result of unreduced pollen and unreduced eggcells in both parents. This bilateral sexual polyploidiation has also been used in a third cycle of crosses, making use of diploid homozygous amf-clones. A second method to achieve tetraploid progeny has been 4x.2x crosses, where only the pollendonor has to form unreduced gametes to get a tetraploid progeny (unilateral sexual polyploidization).

In general the first two or three cycles of this breeding program have been used to produce male and female fertile amf-breeding material, on the diploid level with the ability to produce unreduced gametes, as a start for a breeding program on diploid and tetraploid chromosomal level. In these breeding cycles also properties as tuber shape, number of tubers and starch content where observed, but no stringent selection where carried out.

From the third cycle onwards crosses have been made between homozygous tetraploid amf clones with existing tetraploid starch potato varieties. From these varieties genetic variation with respect to total starch production and resistance against diseases (potato cyst nematode, late blight, wart disease) was introduced. In the second cycle of these crosses made for agronomic improvement segregation of homozygous recessive amf-clones was expected and colouring of tubers with iodine solution was carried out. As a result of this breeding program some agronomical acceptable clones were produced, which are both useful for the large scale production of amylosefree potato starch and as crossing parents in 4x.4x and 4x.2x crosses.

Starch analysis. Starch granules in micropores and tubers were stained with $I_2$-KI solution according to Hovenkamp-Hermelink et al. (1987), in stomatal guard cells and other leaf cells according to the treatment described for, microspores and in root cap cells by treatment of root tips with a mixture of Lugols-solution and choralhydrate (1:1, v/v). Four gram of choralhydrate is dissolved in 2 ml of water. The amylose percentage in starch solutions of tubers was measured according to Hovenkamp-Hermelink et al., 1988, Potato Res. 31:241-246). Roottips were fixed and stained according to Pijnacker and Ferwerda (1985, Can. J. Genet. Cytol. 26:415-419) for chromosome counts and karyotypic investigations. When for example microspores are stained with a potassium iodide solution (Lugol), starch is stained red in mutants (comprising only the amf-gene) and dark blue in the wild type (comprising only the Amf-gene) (Jacobsen et al., 1989, Euphytica 44:43-48).

Protein Analysis

For determining raw and coagulated protein content, 300 grams of tuber material together with 1000 ppm sodium bisulphite was grinded in a laboratory blender, type Waring Blendor. To determine the dry matter content an homogeneous sample of approx. 10 gram was taken and dried overnight at 40° C. The rest of sample was centrifuged for 10 min at 4600 rpm. Of the supernatant raw protein content was determined by determining nitrogen content with the Kjeldahl method and dry matter by overnight drying at 40° C. To determine the coagulated protein content in the supernatant the pH was adjusted to 5.2 with 19% HCl and the liquid was boiled for 1 minute. Subsequently, the samples were centrifuged for 10 ml at 10000 rpm. To remove the light substance the above liquid was filtered over an S&S 595 paper filter. Nitrogen content of the supernatant after the coagulation step was determined by the Kjeldahl method. All experiments were carried out in duplicate.

Raw and coagulated protein content was calculated as follows:

$$\text{Contribution of juice} = \frac{100 - \% \, DrySubstancePulp}{100 - \% \, DrySubstanceJuice}$$

Raw protein=N total×contribution juice×1.5×0.88×6.25

Coagulated protein=(N total−N after coagulation)×6.25×contribution juice×1.5×0.88

(1.5: dilution factor)

(0.88: correction factor)

Embryo culture. Unripe berries were surface sterilized by treatment for 1 minute with 70% alcohol and for 15 minutes with a saturated solution of Ca-hypochlorite, containing a few drops of 1% SDS (sodium dodecylsulphate) solution per 100 ml. The sterilized berries were cut open aseptically. Ovules were collected and cultured on medium EC2 (MS-medium supplemented with $1.10^{-6}$ g/l kinetin, $1.10^{-6}$ g/l LAA, 8 g/l agar and 30 g/l sucrose) as defined by Neal & Topoleski (1983, J. Amer. Soc. Hort. Sci. 108:434-448; 1985 J. Amer. Soc. Hort. Sci. 110:869-873) for embryo culture of tomato. During ovule culture, the integument rapidly attained a brow color and was removed; this was followed later by entire excision of the embryo from the endosperm, as described by Haynes (1959). The excised embryos were also cultured on medium EC2, at 23° C. and 16 h light. The rescued plantlets were propagated and rooted in $MS_{20}$.

Results

Identification of Amf-Gene Mutants

Based on iodine staining of microspores, genotypes corresponding tot nulliplex (no wild-type GBSS-allele), simplex, duplex and triplex/quadruplex for the wild-type GBSS allele were selected. This selection was according to the expected segregation presented in Table 1.

TABLE 1

The expected and obtained offspring when duplex plants (AAaa × AAaa) are crossed. These genotypes can be distinguished after iodine staining by their segregation of blue and red microspores; triplex (AAAa) and quadruplex (AAAA) plants where taken in one group. Genotypes with enough tubers to perform a field trial were selected.

| plant genotype | chance | microspore segregation blue:red | number of genotypes found[a] | number of gynotypes selected |
|---|---|---|---|---|
| aaaa | 1/36 | 0:1 | 3 | 2 |
| Aaaa | 8/36 | 1:1 | 20 | 10 |
| AAaa | 18/36 | 5:1 | 33 | 11 |
| AAAa | 8/36 | 1:0 | 19 | 6 |
| AAAA | 1/36 | 1:0 |  |  | a: $\chi^2$ (1:8; 18:9) = 1.62 < 7.82 which indicates that the offspring is not deviating from the expected 1:8:18:9 segregation of the gene-dosage genotypes for the wild-type GBSS allele.

Starch granules of the duplex and triplex/quadruplex genotypes were completely blue. In some of the simplex genotypes however, a small outer layer was red in a small percentage of the starch granules. A number of tuberising plants belonging to each gene-dosage group was selected for further research in a field trial Table 1).

TABLE 2

The coagulated protein content analysis of offspring when duplex plants (HZ91-RUG-025 × HZ91-RUG-075) are crossed. These genotypes were distinguished after iodine staining by their segregation of blue and red microspores; triplex (AAAa) and quadruplex (AAAA) plants where taken in one group.

| plant genotype | No. individuals | mean | S. E. |
|---|---|---|---|
| aaaa | 15 | 1.51** | 0.08 |
| Aaaa | 15 | 1.22 | 0.06 |
| AAaa | 17 | 1.10 | 0.12 |
| AAAa | 25 | 1.24 | 0.07 |
| AAAA |  |  |  |

**indicates statistically significant effect P < 0.05

TABLE 3

The coagulated protein content analysis of offspring when duplex plants (S90-1103 × S90-1101-0004) are crossed. These genotypes were distinguished after iodine staining by their segregation of blue and red microspores; triplex (AAAa) and quadruplex (AAAA) plants where taken in one group.

| plant genotype | No. individuals | mean | S. E. |
|---|---|---|---|
| aaaa | 8 | 1.67** | 0.08 |
| Aaaa | 18 | 1.38 | 0.07 |
| AAaa | 17 | 1.25 | 0.12 |
| AAAa | 29 | 1.46 | 0.03 |
| AAAA |  |  |  |

**indicates statistically significant effect P < 0.05

GBSS-Protein Content

The amount of GBSS-protein in the starch granule of different genotypes was analyzed. FIG. 1 clearly shows that the amylose-free plants had no GBSS in the starch granules, however no significant difference could be observed in the GBSS-protein level of the other groups indicating that no dosage effect existed at the protein level. No differences in starch granule size and amylopectin and sucrose content of the tubers were found (data no shown)

Overexpression of Heterologous Protein in amf Mutant

The invention furthermore provides a transgenic potato cell with at least one amf-gene having been provided with a nucleic acid encoding a proteinaceous substance, a sin protein. In a preferred embodiment, said cell accumulates said sink protein up to more than 2%, preferably 4%, or even more than 5% to more than 7% of the total protein content of said cell. The protein preferably contains a high content of essential amino acids preferably methionine, cysteine, lysine, threonine, or tryptophane). To allow for an enhanced incorporation of these essential amino acids into a sink protein fraction of the amf potato cell said cell is provided with one or more gene constructs or nucleic acid molecules encoding at least one functional enzyme related to said amino acid's biosynthesis pathway allowing said cell to increasingly synthesise said amino acid, preferably wherein said amino acid is an essential amino acid and thereby further regulates supply. Preferably, free amino acid level is increased by introducing at least one gene encoding a feedback insensitive enzyme involved in biosynthesis of said amino acid. The over-produced free essential amino acids are trapped by incorporation in a sink protein, rich in said essential amino acid that is expressed at the same time in the plant.

As food or feed organisms, or tissues, differ in limiting essential amino acids, the optimal amino acid content for a sink protein varies according to organism. A sink protein preferably is a protein specifically enriched in those amino acids for which a definite occurs in the specific crop or organism. By producing the sink protein to at least 2%, preferably to at least 4%, 5%, or even at least 7% of the total protein content of the tissue which is being used as food or feed, we compensate for the essential limiting amino acid. For example, for potato a sink protein preferably contains at least 5%, more preferably at least 10% lysine, at least 2.5% methionine, at least 2.5% cysteine, or at least 1.6% tryptophan.

The protein is stable in the plant, accumulates to high levels and has no drastic detrimental effects on the growth and physiology of the crop plant. The protein is well digestible by the livestock and/or human digestive tract.

Sink protein candidates can for example be selected from among known storage proteins. Several publications describe the amino acid composition of plant storage proteins, and their possible use to enhance the essential amino acids composition of food and feed crops. The storage proteins of cereal crops like wheat, barley and maize of the so-called prolamin type vary in their content of sulphur-containing amino acids (methionine and cysteine). Some are relatively high in S-rich amino acids. However, most of them are severely deficient in lysine and tryptophan (Shewry, P. R., (1998) Transgenic Plant Research, p. 138-149). The storage proteins in legumes and other dicotyledons are mainly of the globulin family or the albumin family. Globulins are generally very poor in the sulphur containing amino acids, but sometimes do contain a relatively high ratio of lysine. Vicilin (of Vica faba) has a lysine content of 7.2%, threonine content of 3% and a methionine content of only 0.2%. The 2S albumin family of storage proteins in general have a high content of S-rich amino acids. Brazil nut 2S albumin contains ca. 26% sulfur amino acids (Ampe 1986), and sunflower 2S albumin (Sfa8) contains 24% sulfur amino acids (Kortt 1991). Other storage proteins that have a high content of lysine residues are the protease inhibitors C1 and C2 from barley (9.5% and 11.6% lysine respectively, Hejgaard and Boisen (1980)) and the cysteine protease inhibitor multicystatin of potato (Waldron et al., 1993 Plant Mol. Biol. 23(4):801-12).

The level of protein accumulation in a plant is determined by the rate of synthesis in relation to the rate of degradation of this protein. The rate of degradation is determined by its sensitivity to attack of proteases that are present in the producing tissue. This protease sensitivity is influenced by the availability of susceptible sequence domains on the surface of the protein, in combination with the structural rigidity of the protein. In order to select for a protein that will have a high chance to accumulate in the plant, the protein preferably has a rigid tertiary structure, with minimal exposed sequence domains. Certain proteins have a native tendency to aggregate into more or less regular or organized macromolecular structures, such as protein bodies or protein crystals. Naturally, storage proteins that accumulate in plant tissue, where they have a storage function, are naturally adapted to remain stable in these plant tissues. Therefore seed storage proteins are distinct candidates to accumulate essential amino acids. However, few plant storage proteins will always have a desired composition relating to the desired essential amino acids. Furthermore, in general the amount of essential amino acids is often too low. The invention herewith provides using sink protein that is encoded by a nucleic acid enriched with the necessary codons encoding said desired amino acids. In addition to this, in nature several proteins exist that form (semi)-crystaline structures in their natural tissue. Examples are some peroxisomal proteins like alcohol oxidase or urate oxidase, or crystallins (eye lens proteins). Also plant structural proteins are able to form regular crystal like structures, for example the cysteine protease inhibitor multicystatin present in the peel of potato.

As an example the use of a combination of gene constructs containing a DNA sequence encoding an enzyme having dyhydrodipicolinate synthase (DHPS) activity combined with a DNA sequence encoding a sink protein that is rich in essential amino acids, e.g. multicystatin, is provided. First half of this construct containing the DHPS genes results in an increased level of free lysine more than 10-fold the wild type level of each amino acid in a plant or parts thereof. The expression regulation should be such that expression occurs in such a way that lysine are produced to a comparable extent without damaging the plant i.e. without causing negative aberrations in the phenotype compared to wild type plants. The second part of this combination of gene constructs consists of a gene encoding a sink protein, which contains a high amount of essential amino acids. This sink protein results in an increased incorporation of essential amino acids into the protein fraction. As such it withdraws these amino acids from the pool of free amino acids, thus further enhancing the synthesis of these essential amino acids.

Example 1

Chimeric Gene Construct with the Mutant Potato DHPS Gene

DNA isolation, subcloning, restriction analysis and DNA sequence analysis is performed using standard methods (Sambrook, J. et al. (1989) Molecular Cloning. A laboratory manual, Cold Spring Harbor Laboratory Press; Ausubel, F. M. et al. (1994) Current protocols in molecular biology, John Wiley & Sons).

In order to create a feedback insensitive DHPS, the evolutionary conserved amino acid residue 134 (asparagine) were changed into a cysteine residue (WO0148230). The mutant DHPS encoding DNA fragment (designated DEPS-134nc1) was used for the expression in potato plants.

The chimeric gene containing the mutant DHPS gene was constructed by subcloning DHPS cDNA from the pTriplex vector in pCR-cript SK(+) and from this vector as a XbaI-Eco RI fragment in the pBluescript SE vector digested with XbaI-EcoR. With this clone the mutagenesis was performed, resulting in clone pAAP57-134nc1. At the 5' end the mutated DHPS cDNA was fused to a HindIII-SalI fragment of the 800 bp long GBSS promoter fragment (Visser et al. ibid). Downstream of the mutant DHPS sequence the termination signal of the nopaline synthase gene from *Agrobacterium tumefaciens* was inserted (Greve, H. D. et al. (1983) J. Mol. Appl. Genet. 1: 499-511) as an SstI-EcoRI fragment. The complete chimeric gene was subcloned into the HindII-EcoRI sites of pBINPLUS (Van Engelen, F. A. et al. (1995) Transgenic Research 4: 288-290) (pAAP105).

The binary vector pAAP105 was used for freeze-thaw transformation of *Agrobacterium* tumefaciens strain AGLO (Höfgen, R. and Willmitzer, L. (1988) Nucl. Acids Res. 16: 9877). Transformed AGLO was subsequently used for inoculation of potato (*Solanum tuberosum*, variety Kardal) stem explants as described by Visser (Visser, R. G. F. (1991) Plant Tissue Culture Manual B5 (ed. by K. Lindsey): 1-9, Kluwer Acad. Publishers, The Netherlands). After shoot and root regeneration on kanamycin-containing media plants were put in soil and transferred to the greenhouse. Plants regenerated (on kanamycin-free media) from stem explants treated with the *Agrobacterium* strain AGLO lacking a binary vector served as a control.

Example 2

Overexpression of the Potato Multicystatin Gene

The Potato Multicystatin (hereinafter PMC) gene encodes a multidomain cysteine protease inhibitor protein. A genomic clone of the PMC gene (Waldron et al., (1993) Plant Molecular Biology, 23:801-812) was fused at the 5' end to the omega DNA sequence from the coat protein of tobacco mosaic virus (Gallie, D. R. et al. (1987) Nucl. Acids Res. 15: 3257-3273). Downstream of the PMC sequences the termination signal of the octopine synthase gene from *Agrobacterium tumefaciens* is inserted (Greve, H. D. et al. (1988) J. Mol. Appl. Genet. 1: 499-511). The chimeric PMC gene construct is cloned as a BamHI/SpeI fragment in pBluescript. The patatin promoter (Wenzler, H. C. et al. (1989) Plant Mol. Biol. 12: 41-50) is ligated as a blunt (HindIII filled in)/BamHI fragment in front of the PMC chimeric gene digested with SmaI/BamHI (pAAP169).

Example 3

Transformation of Potato Plants

The binary vector pAAP105 and PAAP169 is used for freeze-thaw transformation of *Agrobacterium tumefaciens* strain AGLO (Hofgen, R. and Willmitzer, L. (1988) Nucl. Acids Res. 16: 9877). Transformed AGLO is subsequently used for inoculation of tetraploid wildtype potato (*Solanum tuberosum*, variety Kardal and tetraploid amf mutant KA96-1396 stem explants as described by Visser (Visser, R. G. F. (1991) Plant Tissue Culture Manual B5 (ed. by K. Lindsey): 1-9, Kluwer Acad. Publishers, The Netherlands). After shoot and root regeneration on kanamycin-containing media plants are put in soil and transferred to the greenhouse. Plants regenerated (on kanamycin-free media) from stem explants treated with the *Agrobacterium* strain AGLO lacking a binary vector serve as a control.

Example 4

Analysis of Free No Acid Content in Transgenic Plants

Tissue (0.5-1.0 gram) is homogenized with mortar and pestle in 2 ml 50 mM Pi-buffer (pH 7.0) containing 1 mM dithiothreitol. Nor-leucine is added as an internal standard. Free amino acids are partly purified by extraction with 5 ml of a water:chloroform:methanol mixture (3:5:12). Water phase is collected and the remaining re-extracted twice. After concentration by lyophilization to 3 ml, a 20 mu l sample is analysed by HPLC using a cation-exchange column with post-column ninhydrine derivatisation of the amino acids detected at 570 and 440 nm (BIOCHROM 20, Amersham Pharmacia biotech).

Example 5

Coagulated Protein Content of Transgenic Plants

For determining raw and coagulated protein content, 300 grams of tuber material together with 1000 ppm sodium bisulphite was grinded in a laboratory blender, type Waring Blendor. To determine the dry matter content a homogeneous sample of approx. 10 gram was taken and dried overnight at 40° C. The rest of sample was centrifuged for 10 min at 4600 rpm. Of the supernatant raw protein content was determined by determining nitrogen content with the Kjeldahl method and dry matter by overnight drying at 40° C. To determine the coagulated protein content in the supernatant the pH was adjusted to 5.2 with 19% HCl and the liquid was boiled for 1 minute. Subsequently, the samples were centrifuged for 10 min at 10000 rpm. To remove the light substance the above liquid was filtered over an S&S 595 paper filter. Nitrogen content of the supernatant after the coagulation step was determined by the Kjeldahl method. All experiments were carried out in duplicate.

TABLE 4

| LYSINE RICH | | | | |
|---|---|---|---|---|
| Vicilin | Fava bean | 436 aa | 32 lys (7.2%) | storage protein |
| SCR1 | Soybean | 102 aa | 21 lys (20.6%) | stress induced |
| Fcor 2 | Strawberry | 133 aa | 19 lys (14.3%) | cold induced |

TABLE 4-continued

| TLRP multicystatine | Tomato Potato | 62 aa | 11 lys (17.7%) 11.8% lys | matrix protein Protease inhibitor |
|---|---|---|---|---|
| METHIONINE RICH | | | | |
| γZein | Maize | 211 aa | 55 met (26.1%) | storage protein |
| 10 kDa Zein | | 150 aa | 31 met (20.7%) | storage protein |
| 2S albumin | Sunflower | 141 aa | 18 met (12,8%) | storage protein |
| THREONINE RICH | | | | |
| TIP13 | Asparagus | 182 aa | 23 thr (12.6%) | harvest |
| PTGRP | Tomato | 78 aa | 16 thr (20.5%) | water stress |
| CYSTEINE RICH | | | | |
| PA1b | Pea | 130 aa | 10 cys (7.7%) | storage protein |
| SE60 | Soybean | 47 aa | 8 cys (17.2%) | storage protein |
| PCP1 | Rape Seed | 83aa | 8 cys (9,6%) | pollen/stigma |

The invention claimed is:

1. A method for breeding and selecting a potato having increased protein content comprising
    (a) crossing a first parent potato plant having at least one amf-allele with a second parent potato plant having at least one amf-allele to produce progeny;
    (b) selecting and testing said progeny for the presence of at least one amf-allele and for increased protein content; and
    (c) selecting progeny being homozygous for the amf-allele with a protein content higher than a plant heterozygous for the amf-allele.

2. A method for increasing protein storage in a potato comprising
    (a) crossing a first parent potato plant having at least one amf-allele with a second parent potato plant having at least one amf-allele to produce progeny;
    (b) selecting and testing said progeny for the presence of at least one amf-allele and for increased protein content; and
    (c) selecting progeny being homozygous for the amf-allele with protein content higher than a plant heterozygous for the amf-allele.

3. The method according to claim 2, wherein the protein content of tubers of the selected progeny is at least 0.9% m/m.

4. The method according to claim 3, wherein the protein content of tubers of the selected progeny is at least 1.2% m/m.

5. The method according to claim 4, wherein the protein content of tubers of the selected progeny is at least 1.5% m/m.

6. The method according to claim 2, wherein coagulating protein versus starch ratio of the selected progeny is at least 45 kg/ton.

7. The method according to claim 6, wherein coagulating protein versus starch ratio of the selected progeny is at least 90 kg/ton.

8. The method according to claim 2, further comprising transforming said selected progeny with a gene encoding a heterologous protein.

9. The method according to claim 8, wherein the heterologous protein is selected from the group consisting of DHPS, PMC, vicilin, SCR1, Fcor2, TLRP, multicystatine, yZein, 10 kDa Zein, 2S albumin, TIP13, PTGRP, PA1b, SE60 and PCP1.

* * * * *

UNITED STATES PATENT AND TRADEMARK OFFICE
CERTIFICATE OF CORRECTION

| | | |
|---|---|---|
| PATENT NO. | : 7,880,067 B2 | Page 1 of 1 |
| APPLICATION NO. | : 10/537037 | |
| DATED | : February 1, 2011 | |
| INVENTOR(S) | : Heeres et al. | |

It is certified that error appears in the above-identified patent and that said Letters Patent is hereby corrected as shown below:

Column 5, line 46:

Now reads: "an finale"
Should read: --an female--

Column 8, line 31:

Now reads: "sin protein"
Should read: --sink protein--

Signed and Sealed this
Eleventh Day of September, 2012

David J. Kappos
*Director of the United States Patent and Trademark Office*